US00PP37015P2

(12) United States Plant Patent
Moon

(10) Patent No.: US PP37,015 P2
(45) Date of Patent: Oct. 14, 2025

(54) ***TAXODIUM* PLANT NAMED 'TAMTF'**

(50) Latin Name: *Taxodium ascendens*
Varietal Denomination: TAMTF

(71) Applicant: Dwayne Moon, Washington, GA (US)

(72) Inventor: Dwayne Moon, Washington, GA (US)

( * ) Notice: Subject to any disclaimer, the term of this patent is extended or adjusted under 35 U.S.C. 154(b) by 0 days.

(21) Appl. No.: 19/085,360

(22) Filed: Mar. 20, 2025

(51) Int. Cl.
*A01H 5/00* (2018.01)
*A01H 7/00* (2006.01)

(52) U.S. Cl.
USPC ..... Plt./213

(58) Field of Classification Search
USPC ..... Plt./213
See application file for complete search history.

(56) References Cited

U.S. PATENT DOCUMENTS

PP17,767 P3 * 5/2007 Zengji ..... A01H 7/00
Plt./213

* cited by examiner

*Primary Examiner* — Karen M Redden

(57) ABSTRACT

A new and distinct *Taxodium ascendens* cultivar named 'TAMTF' is disclosed, characterized by a growth habit with a central leader and uniform, uncongested scaffolding of branches. Foliage is dark green foliage. Fall foliage color is greyed-orange. Growth rate is moderate. The new cultivar is a *Taxodium*, suitable for outdoor horticultural purposes.

3 Drawing Sheets

Latin name of the genus and species: *Taxodium ascendens*.

Variety denomination: 'TAMTF'.

BACKGROUND OF THE INVENTION

The new cultivar was discovered in the Fall of 2017 growing as a seedling in a production field in at a tree farm in Washington, Georgia, among a group of cross-pollinated Pond Cypress. In the Winter of 2018, these liners were relocated from the liner field to a production field. It was here that the inventor discovered the claimed cultivar *Taxodium ascendens* 'TAMTF'. Evaluation of this tree continues on the same tree farm located in Washington, Georgia.

*Taxodium ascendens* 'TAMTF' was first asexually propagated by the method of grafting propagation at the inventor's direction in the Winter of 2018 at his farm in Washington, Georgia. The cleft grafting system developed by the inventor has resulted in progeny that have proven the characteristics of my new variety to be genetically stable. This grafting process involved taking cuttings in February, being grafted, and being placed in calloused chambers for approximately three weeks. They are then moved into 3"×6" tree band pots and placed in humidity chambers for approximately four weeks. Furthermore, these observations have confirmed that my new variety represents a new and improved variety of *Taxodium ascendens* tree as particularly evidenced by the dark green foliage, central leader, moderate growth rate and uniformly scaffolding branches. These genetic traits can be consistently reproduced by asexual propagation.

SUMMARY OF THE INVENTION

The cultivar 'TAMTF' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'TAMTF' These characteristics in combination distinguish 'TAMTF' as a new and distinct *Taxodium* cultivar:

1. Dark green foliage.
2. Central leader.
3. Moderate growth rate of approximately 1 inch of caliper per year.
4. Uniform, uncongested scaffolding of branches

COMPARISON TO PARENT VARIETY

The exact parent varieties cannot be identified.

COMMERCIAL COMPARISON

*Taxodium* 'TAMTF' can be compared to the commercial variety *Taxodium ascendens* 'Morris', (US20050108799). Plants are similar in most horticultural characteristics, however, plants of the new variety differ in the following:

1. 'TAMTF' is broader in growth habit and structure than this comparator.
2. 'TAMTF' has darker green foliage than this comparator.
3. Left unpruned 'TAMTF' has less congested branching than this comparator.

BRIEF DESCRIPTION OF THE PHOTOGRAPHS

The accompanying photograph in FIG. 1 illustrates in full color a typical tree of 'TAMTF' grown outdoors in Washington, GA during summer. The tree is approximately 4 years old, shown growing in the ground.

Figure 1:
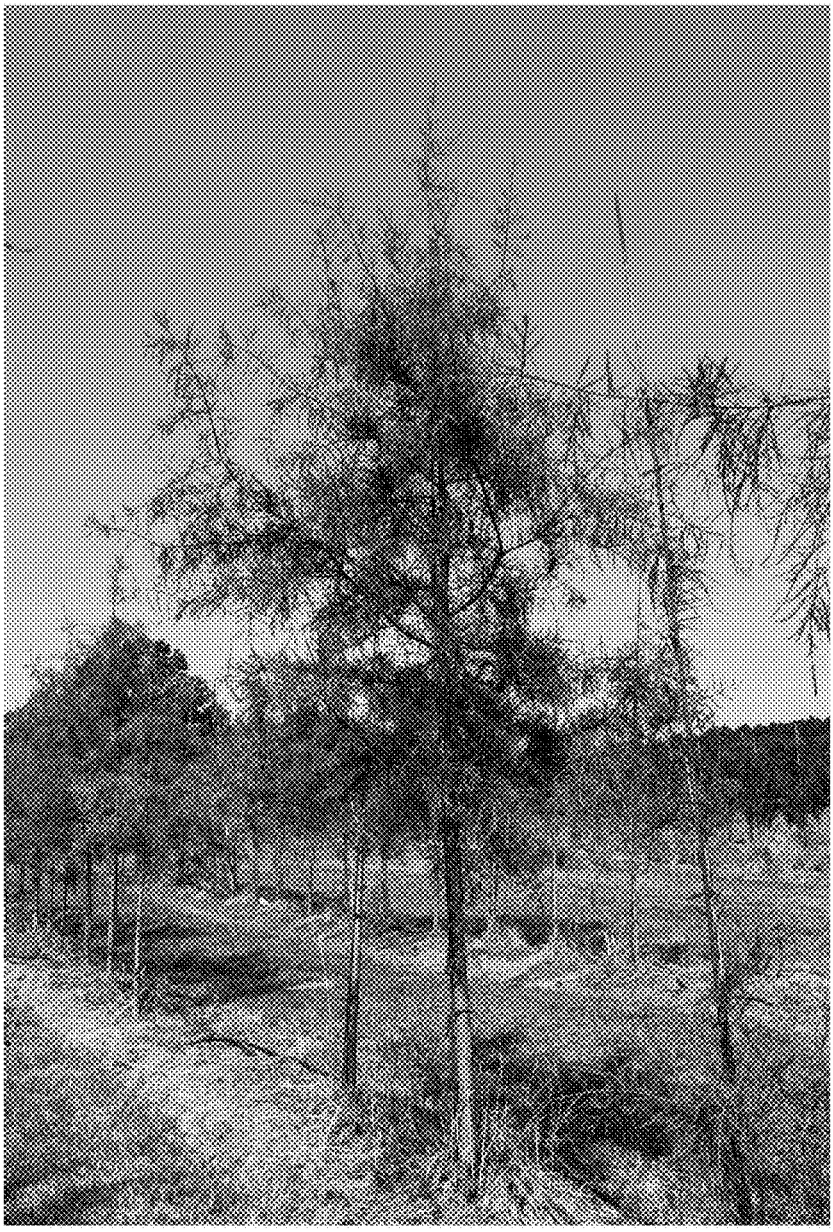
Figure 2:
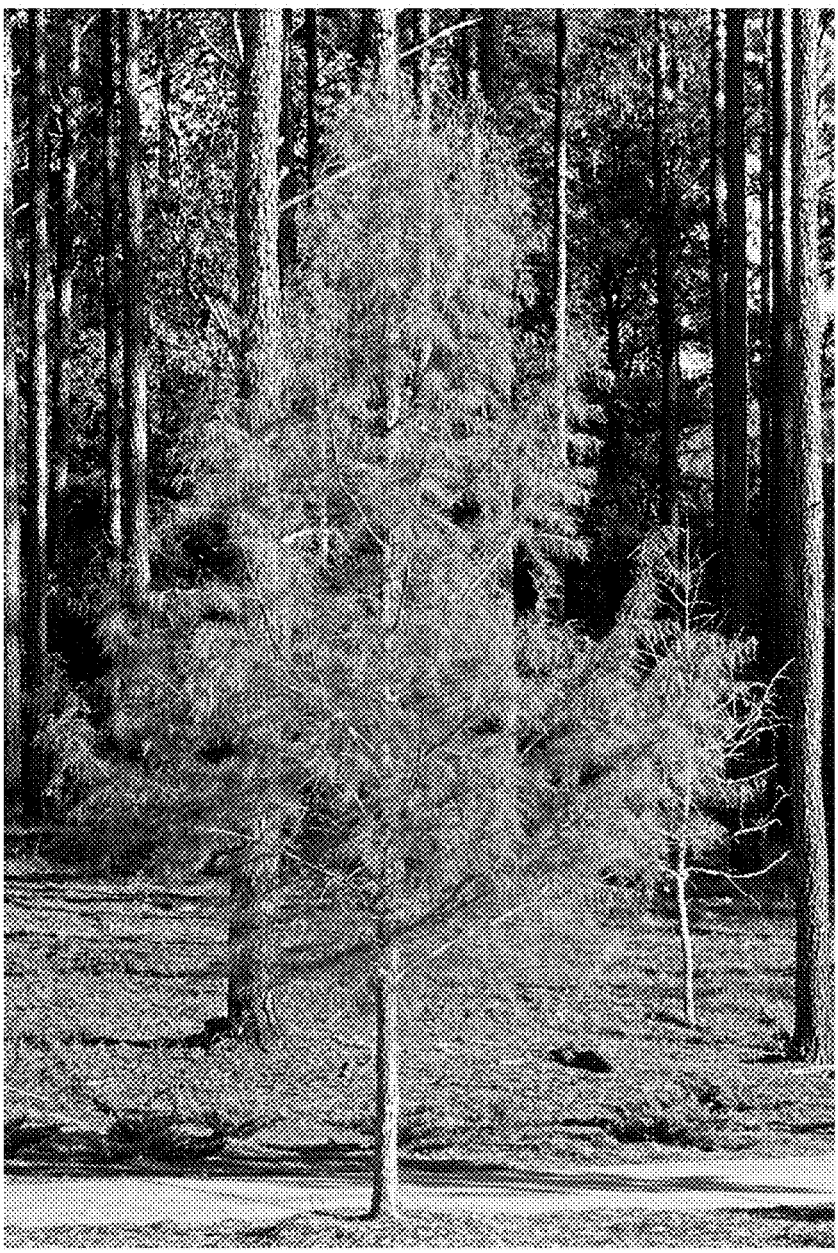
FIG. 2 illustrates in full color the fall foliage color on a typical tree of 'TAMTF' grown outdoors in Washington, GA.
Figure 3:
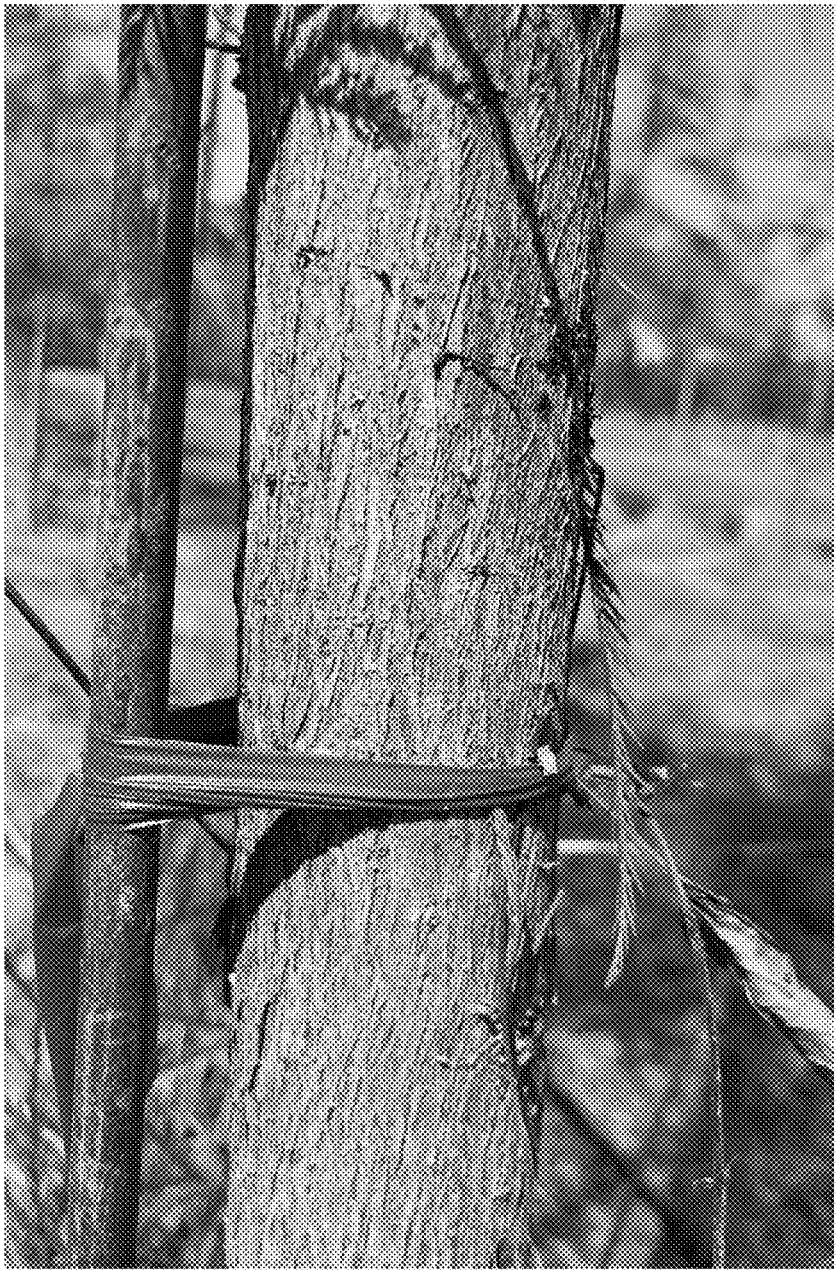
FIG. 3 illustrates a close-up of typical bark of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'TAMTF' plants grown outdoors in Washington, Georgia. Plants are approximately 2-3 years old, in a 3 gallon nursery container unless otherwise noted. Measurements and numerical values represent averages of typical plant types.

Botanical classification: *Taxodium ascendens* 'TAMTF'.

PLANT

Growth habit: Upright deciduous tree with an open, non-congested scaffolding.

Height: About 12 to 14 feet at 3 years.

Plant spread: About 6 to 8 feet at 3 years.

Typical growth rate: Moderate to rapid.

Trunk characteristics:

- *Diameter*.—About 3.5 inches measured at approximately 3 inches above soil level at 3 years.
- *Color*.—Trunk Greyed-Orange 175A and 172B. Peeling bark color Grey-Brown 199D.
- *Surface texture*.—Moderately shaggy.

Branching habit: Even and uniform scaffolding, not congested. Main branches occurring at angles of 60 to 75 degrees from center.

Length of lateral branches: About 120 to 250 cm.

Average number of lateral branches: About 15 to 20 main branches.

Diameter of lateral branches: About 20 mm.

Lateral branch color: Near RHS Greyed-Orange 177A. Scales, peeling colored Grey-Brown 199A.

Lateral branch strength: Strong.

FOLIAGE

Leaf:

- *General description*.—Soft, feathery and dense. No prickles and no spines.
- *Arrangement*.—Alternate.
- *Shape*.—Awl.
- *Average length*.—4 to 9 mm.
- *Average width*.—1 to 1.5 mm.
- *Apex*.—Rounded.
- *Base*.—Truncate.
- *Margin*.—Entire.
- *Texture of top surface*.—Glabrous.
- *Texture of bottom surface*.—Glabrous.
- *Color*.—Young foliage upper side: RHS Green 137B. Young foliage under side: RHS Green 137B. Mature foliage upper side: RHS Green 137A flushed 147A. Mature foliage under side: RHS Green 137D flushed 147A. Fall foliage upper side: RHS Greyed-Orange 167C flushed 168A and 168B. Fall foliage under side: RHS Greyed-Orange 167C flushed 168A and 168B.
- *Venation*.—Indistinguishable from leaf blade.

FLOWER

Flowering and cones not observed to date.

OTHER CHARACTERISTICS

Disease and pest resistance: Neither resistance no susceptibility to normal diseases and pests of *Taxodium ascendens* observed.

Drought tolerance: No tolerance for drought observed. Wet soils well tolerated.

Temperature tolerance: USDA Zones 5-9.

What is claimed is:

1. A new and distinct cultivar of *Taxodium* plant named 'TAMTF' as herein illustrated and described.

* * * * *